United States Patent [19]

Carls et al.

[11] Patent Number: 4,760,203

[45] Date of Patent: Jul. 26, 1988

[54] PROCESS FOR THE PRODUCTION OF ISOPROPYL ALCOHOL

[75] Inventors: Rolf-Rainer Carls, Duisburg; Günther Osterburg, Rheurdt; Milan Prezelj, Frankfurt am Main; Werner Webers, Rheinberg, all of Fed. Rep. of Germany

[73] Assignee: Deutsche Texaco Aktiengesellschaft, White Plains, N.Y.

[21] Appl. No.: 86,431

[22] Filed: Aug. 18, 1987

[30] Foreign Application Priority Data

Aug. 19, 1986 [DE] Fed. Rep. of Germany ....... 3628007

[51] Int. Cl.⁴ ............................................. C07C 29/06
[52] U.S. Cl. .................................................. 568/899
[58] Field of Search ........................................ 568/899

[56] References Cited

U.S. PATENT DOCUMENTS

| | | | |
|---|---|---|---|
| 4,012,456 | 3/1977 | Chaplits | 568/899 |
| 4,087,471 | 5/1978 | Bowman et al. | 568/899 |
| 4,180,688 | 12/1979 | Imaizumi et al. | 568/899 |
| 4,182,920 | 1/1980 | Giles et al. | 568/899 |
| 4,307,257 | 12/1981 | Sada et al. | 568/899 |
| 4,579,984 | 4/1986 | Neier et al. | 568/899 |

Primary Examiner—J. E. Evans
Attorney, Agent, or Firm—Robert A. Kulason; Robert B. Burns; James J. O'Loughlin

[57] ABSTRACT

A direct hydration process for the production of isopropyl alcohol by reacting a propene-containing hydrocarbon stream with an aqueous stream in an interconnected series of reactors in the presence of an acidic cation exchange resin catalyst wherein the improvement comprises charging a propene-containing hydrocarbon stream to one end of a series of interconnected reactors and charging an aqueous stream to the opposite end of a series of interconnected reactors and directing the streams through the series of reactors so that the hydrocarbon stream and the aqueous stream flow in opposite directions with respect to the series of interconnected reactors and flow in parallel streams through each individual reactor is provided.

9 Claims, 3 Drawing Sheets

PROCESS FOR THE PRODUCTION OF ISOPROPYL ALCOHOL

BACKGROUND OF THE INVENTION

This invention relates to a direct hydration process for the production of isopropyl alcohol by reacting a propene-containing hydrocarbon stream with water in the presence of a strongly acidic, solid hydration catalyst, preferably a cation exchange resin catalyst.

DISCLOSURE STATEMENT

DE-AS No. 1 210 768 discloses a process for the continuous production of isopropyl alcohol and diisopropyl ether by the catalytic hydration of propene. In this process, a strongly acidic cation exchange resin consisting of a styrene polymerizate crosslinked with about 5 to 20 wt. percent divinyl benzene and containing about one sulfonic acid group per aromatic ring is used as a catalyst. In this process, a pressure of about 17 to 105 atm., a temperature of about 135° to 157° C., and a water/propene mole ratio of 4 to 10:1 is employed to produce the alcohol product. Feed rates from 0.5 to 10 parts by vol. of liquid propene per part by vol. of moist catalyst resin per hour are disclosed. Since the density of liquid propene at the saturation pressure $d_4^{20}$ is 0.51934 g/ml, this feed rate corresponds to about 6.7 to 123.4 moles of propene per liter of catalyst an hour. In this process, 20 to 90 mole percent of the propene feed are reported to be converted per pass with a conversion rate of about 35 percent being preferred. Under these conditions the best selectivity for isopropyl alcohol (IPA) was attained at 135° C., but this was only 69 mole percent of the propene converted only at 22 mole percent.

The selectivity for the byproducts was about 28 and 3 mole percent for diisopropyl ether and propene polymerizates, respectively.

The relatively low degree of olefin conversion increases slightly at higher operating temperatures but the formation of polymerizate increases and the selectivity for IPA decreases. Moreover, a temperature of more than about 149° C. was found to be detrimental to catalyst life. It was difficult to keep the temperature fluctuations in the catalyst layer within a range of about 11° C., particularly at higher conversion rates. It was attempted to overcome the difficulties caused by local overheating of the catalyst by using relatively high water/olefin mole ratios ranging from about 4 to 10:1.

DE-AS No. 1 105 403 discloses a process in which a sulfonated mixed polymerizate of about 88 to 94 percent styrene and 12 to 6 percent p-divinyl benzene was used as a catalyst containing 12 to 16 wt. percent sulfur in the form of sulfonic acid groups and in which 25 to 75 percent of the protons of these acid groups had been replaced by metals of the groups I or VIII of the periodical system, particularly Cu. This patent discloses that an acceptable selectivity for IPA is attained at a lower temperature, i.e. about 120° C., and a low conversion degree, about 3.9 mole percent. At a higher temperature (170° C.) the propene conversion increased to about 35 mole percent, but the selectivity for IPA decreased to 55 percent and the IPA contained about 45 percent diisopropyl ether. Due to the low selectivity for IPA, this process is not competitive.

U.S. Pat. No. 4,340,769 discloses a process for the production of IPA in a reactor designed as a trickle column, propylene and water being fed as parallel currents. In this process, the conversion rate of the propene is 75 percent necessitating propene recovery from the residual gas stream. The selectivity or IPA is about 95 percent.

U.S. Pat. No. 3,994,983 discloses a process for isopropyl alcohol in which propene and water are charged to the sump of a reactor and passed through the reactor in parallel currents. Propene conversion is about 10 percent per pass but the selectivity is as high as 99 percent which decreases to less than 95 percent if the supercritical gas phase is loaded with about 20 percent IPA. The principle drawback of this process is that the lower total conversion necessitates reconcentration of the residual gas.

Processes for improving the selectivity for IPA are known which suppress establishment of the equilibrium by recycling the formed ether to the feed stream, see e.g. Chemical Engineering, Sept. 4, 1972, p. 50, 51 and U.S. Pat. No. 4,581,475.

Alternative methods for increasing the total selectivity of a continuous process either by splitting of the ether either into the initial olefin and alcohol or into two molecules of alcohol per mole of ether in the presence of excess water are known see U.S. Pat. No. 4,352,945 and U.S. Pat. No. 4,581,475.

The ether recycling or splitting alternatives have the disadvantage of requiring an additional reactor. Moreover, the first alternative mentioned specifies the recycling of ether to the feed stream which causes reactor efficiency to decrease significantly.

It is an object of this invention to provide a process for the production of IPA in good yield and selectivity by the direct hydration of propene without recycling of ether to the feed stream to the reactor.

SUMMARY OF THE INVENTION

In accordance with this invention, isopropyl alcohol is prepared in a direct hydration process by reacting a propene-containing hydrocarbon stream with water or an aqueous stream in an interconnected series of reactors or reaction zones in the presence of an acidic cation exchange resin catalyst by charging the propene-containing hydrocarbon stream to one end of the series of interconnected reactors and charging an aqueous stream to the opposite end of the series of interconnected reactors so that the hydrocarbon stream and the aqueous stream flow in opposite directions with respect to the series of interconnected reactors and flow in parallel streams through each individual reactor or reaction zone.

DETAILED DESCRIPTION OF THE INVENTION

Figure 1:
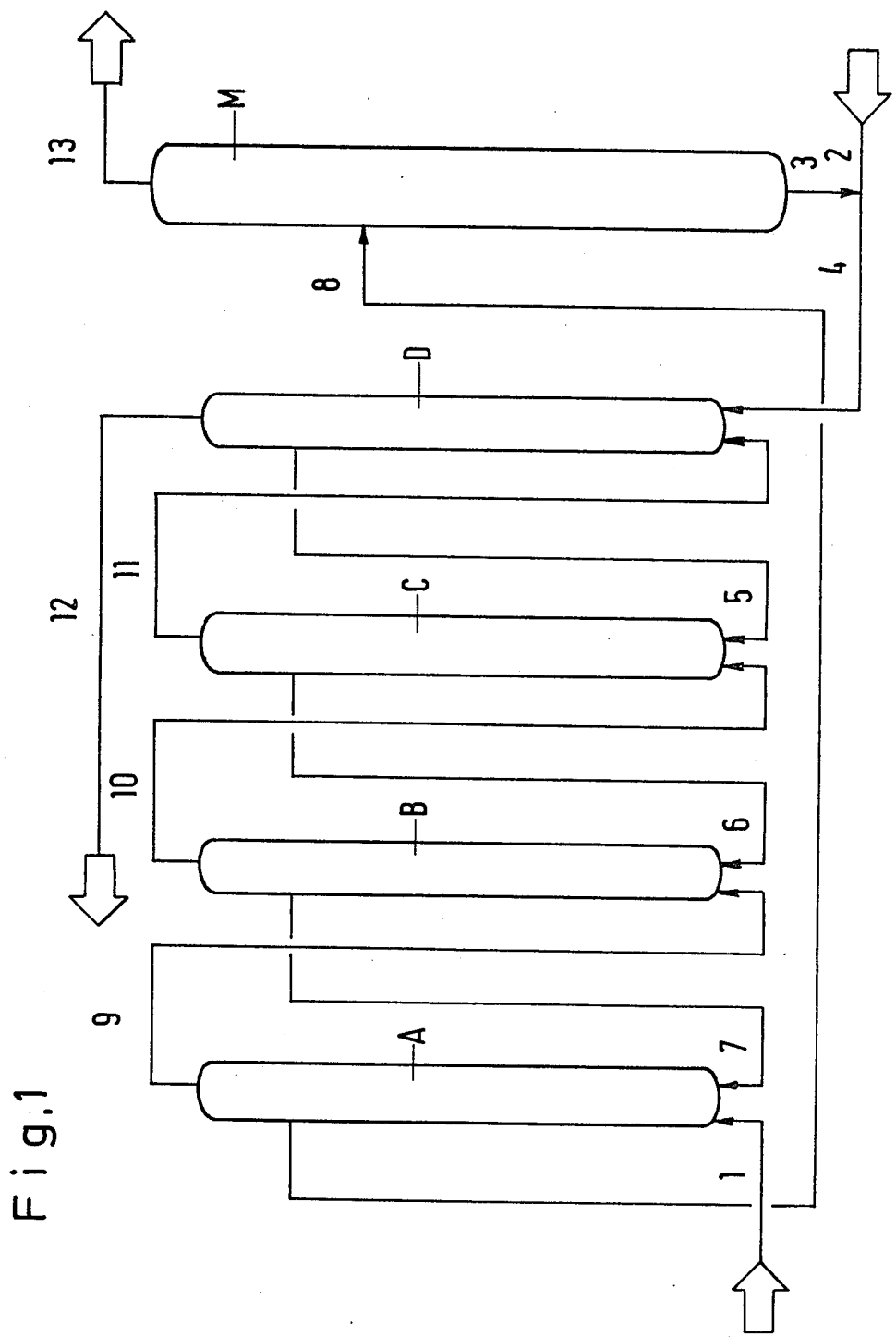

The present invention provides a process for the production of isopropyl alcohol in which propene or a propene-containing hydrocarbon mixture is reacted with water in the presence of a hydration catalyst, particularly a cation exchange resin of the sulfonic acid type. The process is conducted by charging the propene-containing hydrocarbon stream to the inlet of the first reactor and the process water to the inlet of the last reactor in a series of two or more reactors. In the individual reactors, the process water and the hydrocarbon stream form parallel currents, but relative to the entire reactor system, the hydrocarbon stream flows or is cascaded from the first reactor to the last one while in countercurrent thereto the process water flows or is cascaded from the last reactor to the first.

Examples of the embodiment of the invention are shown in the drawings and are described in detail in the following. The figures show:

FIG. 1 Flowsheet of the sump process of the invention

Figure 2:
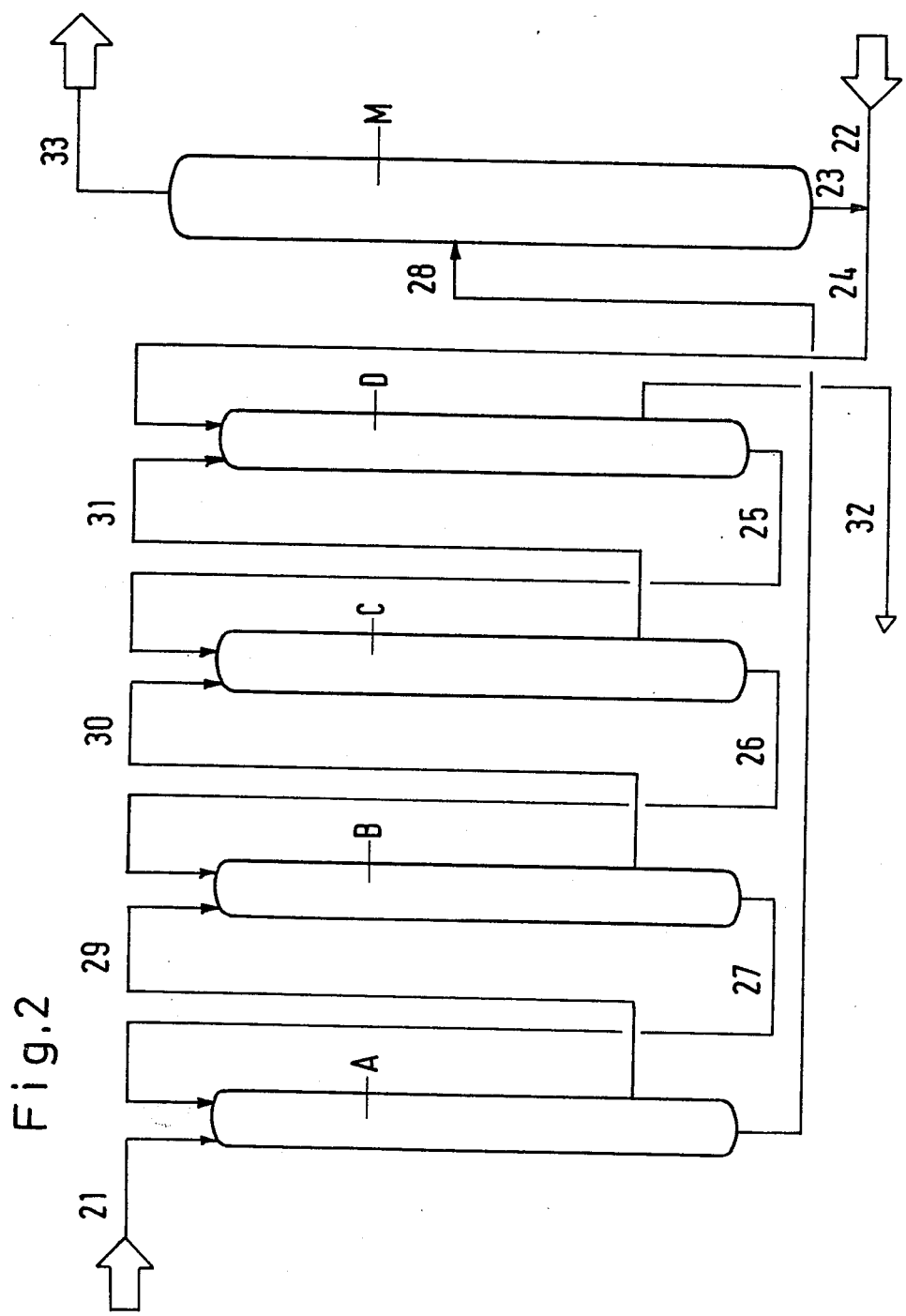

FIG. 2 Flowsheet of the trickle process of the invention

Figure 3:
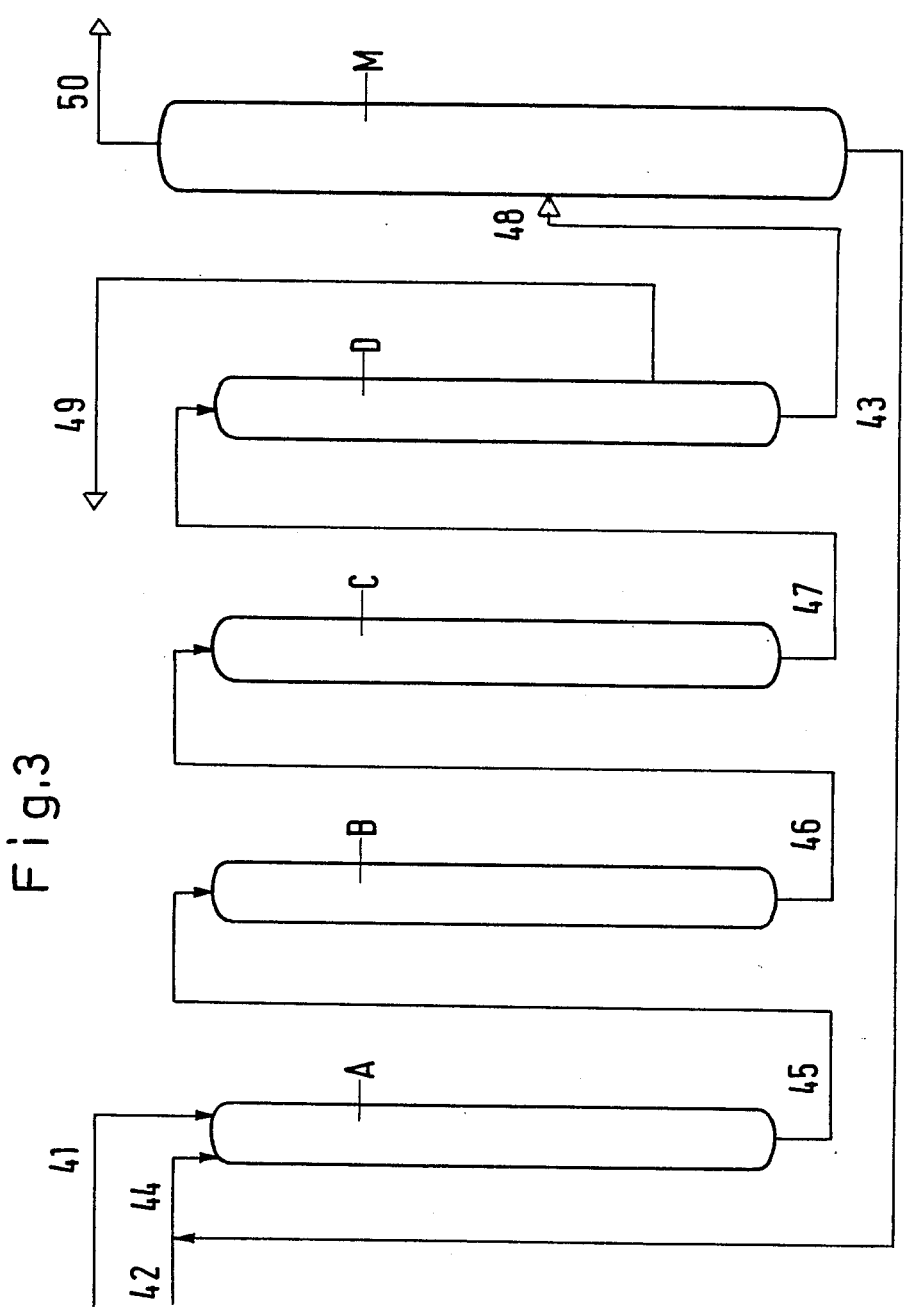

FIG. 3 Flowsheet of the parallel current trickle process according to the prior art In the sump process according to FIG. 1 with a reactor system consisting of 4 reactors A, B, C, D, a propene-containing hydrocarbons mixture ($C_3$ cut) is fed through line 1 to the sump of reactor A. Process water is united through line 2 with the excess process water from the sump of column M (line 3) and is fed through line 4 to the sump of the last reactor D. The aqueous phase withdrawn through line 5 in the top zone of reactor D is fed to the sump of reactor C, is led through lines 6 and 7 to the reactors B and A, resp., and is finally led through line 8 to column M.

The hydrocarbons stream withdrawn through line 9 at the top of reactor A is fed to the sump of reactor B and then through lines 10 and 11 to the reactors C and D, resp., and is finally removed through line 12 as residual gas.

This means that the process water and the propene-containing hydrocarbon flow through the individual reactors as parallel currents, but that they are cascaded through the line of reactors as countercurrents.

The process of the invention can also be performed as a countercurrent trickle process. An embodiment is depicted in FIG. 2 using the same reactor system with 4 reactors. In this process a propene-containing hydrocarbons mixture ($C_3$ cut) is fed through line 21 to the top of reactor A and the process water is fed through line 24 to the top of reactor D, and the process streams are cascaded as countercurrents through the reactor system.

The process water charged to reactor D is withdrawn as an aqueous phase through line 25, is charged to the top of reactor C, and is then fed through lines 26 and 27 to the preceding reactors B and A, resp. Accordingly, the hydrocarbons stream is withdrawn in the opposite direction in the sump zone of reactor A, is charged through lines 29, 30, 31 to the following reactors B, C, C, resp., and is finally removed through line 32 as residual gas.

Aqueous IPA is withdrawn through lines 8 and 28, resp., either from the top zone (sump process) or from the sump (trickle process) of reactor A and is fed to column M, azeotropic IPA being obtained at the top of the column through line 13 or 33. If required, the azeotropic alcohol can be dried in a conventional way.

According to a preferred embodiment of the process, the reaction temperature in four reactors connected in series is chosen such that almost complete conversion of propene (99 percent) and about 99 percent selectivity are attained.

Either sump operation in which the hydrocarbons stream and the process water are fed to the sump of the respective reactors, or trickle operation in which the two process streams are fed to the top of the respective reactors is possible. The process of the invention is preferably performed in a reactor system consisting of 2 to 10 reactors, particularly 3 to 5.

Following the same mode of operation, the process of the invention can also be performed in a single reactor having several reactor beds as separate reaction zones, one process stream being led from the top to the bottom and the other process stream being led from the bottom to the top, and while in the sump phase process the process streams are fed to the sump of the respective zone and in the trickle process they are fed to the top of the respective zone, the individual reaction zones are flown through by parallel streams. In order to remove the alcohol, it is advantageous to wash the hydrocarbons stream leaving the reactor system with water and to charge this water as process water to the reactor.

At the top of the first reactor an aqueous isopropyl alcohol is withdrawn which is concentrated by distillation. The alcohol obtained has a purity of 99 to 99.9 percent, depending on the reaction conditions. It contains only small amounts of diisopropyl ether (DIPE) (0.1 to 0.2 percent), relative to the 100 percent alcohol. The larger amount of the ether (DIPE)—about 0.4 to 0.6 percent, relative to the amount of alcohol formed—is phased out from the reactor together with the residual gas stream.

The residual gas contains only small amounts of propene such that recovery is no longer necessary.

The process can also be performed as a trickle process according to one mode of operation. The propene-containing hydrocarbons stream is fed to the top of the first reactor. The process water is fed to the top of the last reactor and is withdrawn from the sump of this reactor after decomposition into phases, and is fed in opposite direction to the hydrocarbons stream to the top of the next reactor. The aqueous crude alcohol is finally obtained in the sump of the first reactor and is concentrated by distillation. From the sump of the last reactor, a residual gas is withdrawn that contains a minor amount of propene.

The process of the invention is performed under conventional conditions. The temperature employed is from 120° to 200° C., preferably 130° to 170° C. The reaction pressure is 60 to 200 bar, preferably 80 to 120 bar. The water/propene mole ratio is 1–50:1, preferably 10–30:1. The LHSV is 0.2 to 3 hours$^{-1}$, preferably 0.5 to 1 hour$^{-1}$.

The process of the invention has the advantage that almost quantitative conversion of any propane/propene mixture, be it a 50 percent or a 98 percent mixture, is possible without reconcentration of the residual gas. As a result of the countercurrent operation prescribed, the process is very selective even under extreme reaction conditions (e.g. at temperatures of higher than 150° C.). Contrary to known parallel current trickle processes, very little isopropyl alcohol and diisopropyl ether is phased out from the reactor system together with the residual gas.

In the process of this invention olefin and water in counterflow are cascaded through the reaction zones. Using this process, the disadvantages of parallel flow operation, namely requirement of high olefin concentration in the feed gas insufficient olefin conversion poor selectivity can be overcome making aftertreatment superfluous.

The advantages of the counterflow operation according to the process of this invention can be achieved not only when a new plant is erected or when an existing parallel flow process is completely revamped, but also by conversion of existing parallel flow reactors in counterflow reactors or by adding 2 to more counterflow reactors where the residual gas discharged from the parallel flow reactors and still laden with a great quantity of olefins and byproducts is converted such that an olefin conversion of 98 to 99%, a selectivity of 99%, and a satisfactory reactor efficiency are attained without aftertreatment.

Thus, the same objective as with a separate counterflow process is attained, but with less investment.

For the combined parallel flow/counterflow process any solid catalyst system suitable for the direct hydration of olefins can be used. It is also possible to combine other catalyst systems used in parallel flow processes with the acidic cation exchange resin preferred here in the counterflow process.

The following examples illustrate the invention.

EXAMPLES 1 THROUGH 5

In the process depicted in FIG. 1 5,320 g (moist) of a commercial strongly acidic cation exchange resin were distributed over four reactors. A propane/propene mixture was fed via line 1 to the first reactor (A). Process water was charged via stream 4 to the last reactor (D). The water passed through the reactors as a cascade from the last reactor (D) to the first (A). Material flows, operating conditions, and results have been compiled in Table I.

TABLE I

| | Examples | | | | |
|---|---|---|---|---|---|
| | 1 | 2 | 3 | 4 | 5 |
| Temperature, °C. | 150 | 150 | 150 | 158 | 158 |
| Pressure, bar | 100 | 100 | 100 | 100 | 100 |
| Propene content, mole % | 92 | 92 | 92 | 92 | 58 |
| Propane content, mole % | 8 | 8 | 8 | 8 | 42 |
| Process water quantity (Stream 4), g/h | 8000 | 10000 | 10000 | 10000 | 6000 |
| Propane/propene mixture quantity (Stream 1), g/h | 800 | 800 | 1000 | 1000 | 1000 |
| Propene quantity, mole/h | 17.5 | 17.5 | 21.9 | 21.9 | 13.8 |
| Conversion, mole % | 96.7 | 99.6 | 90.8 | 99.3 | 98.3 |
| Selectivity for IPA, mole % | 99.5 | 99.4 | 99.0 | 99.3 | 98.9 |
| Selectivity for IPE, mole % | 0.5 | 0.6 | 1.0 | 0.7 | 1.1 |
| Selectivity for isohexenes plus n-propyl alcohol (NPA) mole % | 0.1 | <0.1 | <0.1 | <0.1 | <0.1 |
| Catalyst efficiency, mole of IPA/1 cat. × h | 2.4 | 2.5 | 2.8 | 3.1 | 1.9 |
| DIPE in residual gas, (unwashed) g/h | 3.4 | 4.0 | 8.1 | 5.9 | 6.0 |

EXAMPLES 6 THROUGH 8

The process of the invention can also be carried out as a trickle process. An embodiment is depicted in FIG. 2.

In this process the propane/propene hydrocarbons stream is fed through line 21 to the top of the first reactor (A) and the process water is fed through line 24 to the top of the last reactor (D). The aqueous alcohol withdrawn from the sump of the first reactor (A) is removed via line 28 and is concentrated in the conventional way.

The four reactors were filled with 5,320 g of a strongly acidic cation exchange resin. Materials flows, operating conditions, and results have been compiled in Table II.

TABLE II

| | Examples | | |
|---|---|---|---|
| | 6 | 7 | 8 |
| Temperature, °C. | 150 | 150 | 158 |
| Pressure, bar | 100 | 100 | 100 |
| Propene content in the C3 hydrocarbons mixture, mole % | 92 | 92 | 58 |
| Process water quantity (Stream 24), g/h | 8000 | 10000 | 6000 |
| C3 hydrocarbons quantity (Stream 21), g/h | 800 | 1000 | 1000 |
| Propene quantity mole/h | 17.5 | 21.9 | 13.8 |
| Conversion, mole % | 97.2 | 92.9 | 98.5 |
| Selectivity for IPA mole % | 99.4 | 99.1 | 98.5 |
| Selectivity for IPE, mole % | 0.6 | 0.9 | 1.5 |
| Selectivity for isohexenes plus n-propyl alcohol mole % | <0.1 | <0.1 | <0.1 |
| Catalyst efficiency, mole of IPA/1 cat. × h | 2.4 | 2.9 | 1.9 |
| DIPE in residual gas, (unwashed) g/h | 4.1 | 7.4 | 8.5 |

EXAMPLES 9 THROUGH 11

(Comparison Examples)

The reactors depicted in FIG. 3 were operated as parallel current trickle reactors under the operating conditions described in the Examples 6 through 8.

Materials flows, operating conditions, and results have been compiled in Table III.

TABLE III

| | Examples | | |
|---|---|---|---|
| | 9 | 10 | 11 |
| Temperature, °C. | 150 | 150 | 158 |
| Pressure, bar | 100 | 100 | 100 |
| Propene content, % | 92 | 92 | 58 |
| Process water quantity (Stream 44), g/h | 8000 | 10000 | 6000 |
| Propane/propene quantity (Stream 41), g/h | 800 | 1000 | 1000 |
| Propene quantity, mole/h | 17.5 | 21.9 | 13.8 |
| Conversion, mole % | 74 | 78 | 59 |
| Selectivity for IPA, mole % | 91.2 | 91.2 | 87 |
| Selectivity for IPE, mole % | 8 | 8 | 12 |
| Selectivity for isohexenes plus n-propyl alcohol mole % | 0.8 | 0.8 | 1.0 |
| Catalyst efficiency, mole of IPA/1 cat. × h | 1.7 | 2.2 | 1.0 |
| DIPE in residual gas, (unwashed) g/h | 60 | 81 | 57 |

EXAMPLES 12 THROUGH 14

(Comparison Examples)

Accordingly, the four reactors were operated as parallel current sump reactors under the operating conditions described in the Examples 6 through 8.

Materials flows, operating conditions, and results have been compiled in Table IV.

TABLE IV

| | Examples | | |
|---|---|---|---|
| | 12 | 13 | 14 |
| Temperature, °C. | 150 | 150 | 158 |
| Pressure, bar | 100 | 100 | 100 |
| Propene content, % | 92 | 92 | 58 |
| Process water quantity g/h | 8000 | 10000 | 6000 |
| Propane/propene quantity g/h | 800 | 1000 | 1000 |
| Propene quantity, mole/h | 17.5 | 21.9 | 13.8 |
| Conversion, mole % | 72 | 74 | 58 |
| Selectivity for IPA, mole % | 92.4 | 92.4 | 88 |
| Selectivity for IPE, mole % | 7 | 7 | 11 |

TABLE IV-continued

| | Examples | | |
|---|---|---|---|
| | 12 | 13 | 14 |
| Selectivity for isohexenes plus NPA mole % | 0.6 | 0.6 | 0.8 |
| Catalyst efficiency, mole of IPA/1 cat. × h | 1.7 | 2.1 | 1.0 |
| DIPE in residual gas, (unwashed) g/h | 51 | 66 | 52 |

The foregoing examples demonstrate the surprising improvement in yield and selectivity that is realized from the novel process of the instant invention for converting propene to isopropyl alcohol.

We claim:

1. In a direct hydration process for the production of isopropyl alcohol by reacting a propene-containing hydrocarbon stream with an aqueous stream in an interconnected series of reactors or reaction zones in the presence of a strongly acidic, solid hydration catalyst, the improvement which comprises charging said propene-containing hydrocarbon stream to one end of said series of interconnected reactors and charging said aqueous stream to the opposite end of said series of interconnected reactors and directing said streams through said series of reactors so that the hydrocarbon stream and the aqueous stream flow in opposite directions with respect to the series of interconnected reactors and flow in parallel streams through each individual reactor.

2. A process according to claim 1 in which said reaction is conducted in a series of 2 to 10 interconnected reactors.

3. A process according to claim 1 in which said reaction is conducted in a series of 3 to 5 interconnected reactors.

4. A process according to claim 1 in which said hydrocarbon stream is fed to the sump of the first reactor in said series and said aqueous stream is fed to the sump of the last reactor in said series and an aqueous stream is withdrawn from the upper zone of each reactor and is fed to the sump of the preceding reactor and a hydrocarbon stream is withdrawn from the top of each reactor and fed to the sump of the following reactor.

5. A process according to claim 1 in which said hydrocarbon stream is fed to the top of the first reactor in said series and said aqueous stream is fed to the top of the last reactor in said series and an aqueous stream is withdrawn from the sump of each reactor and is fed to the top of the proceding reactor, and a hydrocarbon stream is withdrawn from the lower zone of each reactor and is fed to the top of the following reactor.

6. A process according to claim 1 in which said process is conducted in a vertical column having a plurality of reaction zones located one above the other.

7. A process according to claim 1 in which said reaction is conducted at a temperature in the range of 120° to 200° C. and a pressure ranging from about 60 to 200 bar.

8. A process according to claim 1 in which said reaction is conducted in the presence of an acidic cation exchange resin catalyst.

9. In a direct hydration process for the production of isopropyl alcohol by reacting a propene-containing hydrocarbon stream with an aqueous stream in an interconnected series of reactors or reaction zones in the presence of an solid acidic hydration catalyst, the improvement which comprises operating with two series of interconnected reactors and first charging said propene-containing hydrocarbon stream as well as a first aqueous stream to one end of the first series of reactors in parallel flow and then charging the residual gas still containing propene of the first series of reactors to one end of the second series of reactors and charging a second aqueous stream to the opposite end of said second series of reactors and directing said streams through said series of reactors so that the hydrocarbon stream and the second aqueous stream flow in opposite directions with respect to the second series of interconnected reactors and flow in parallel streams through each individual reactor.

* * * * *